United States Patent
Linares et al.

(10) Patent No.: US 9,539,097 B2
(45) Date of Patent: *Jan. 10, 2017

(54) HIP AND KNEE JOINT ASSEMBLIES INCORPORATING DEBRIS COLLECTION ARCHITECTURE BETWEEN THE BALL AND SEAT INTERFACE

(71) Applicant: Linares Medical Devices, LLC, Auburn Hills, MI (US)

(72) Inventors: Miguel A. Linares, Bloomfield Hills, MI (US); Miguel A. Linares, Jr., Bloomfield Hills, MI (US); Ryan T. Greene, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/283,795

(22) Filed: May 21, 2014

(65) Prior Publication Data
US 2014/0296991 A1     Oct. 2, 2014

Related U.S. Application Data

(63) Continuation-in-part of application No. 12/776,903, filed on May 10, 2010, now Pat. No. 8,828,088, and a
(Continued)

(51) Int. Cl.
*A61F 2/30* (2006.01)
*A61F 2/32* (2006.01)
*A61F 2/38* (2006.01)

(52) U.S. Cl.
CPC ............ *A61F 2/30* (2013.01); *A61F 2/30771* (2013.01); *A61F 2/32* (2013.01); *A61F 2/38* (2013.01);
(Continued)

(58) Field of Classification Search
CPC ............... A61F 2002/3408; A61F 2/30; A61F 2002/3433; A61F 2002/30682; A61F 2002/30683; A61F 2002/30685; A61F 2002/30686
(Continued)

(56) References Cited

U.S. PATENT DOCUMENTS 2,667,644 A    2/1954  Johnson
3,651,521 A    3/1972  Devas
(Continued)

FOREIGN PATENT DOCUMENTS

JP        7116184        9/1995

OTHER PUBLICATIONS

International Search Report—Written Opinion—International application No. PCT/US2011/042624, 9 pages.

*Primary Examiner* — Christian Sevilla
*Assistant Examiner* — Seema Mathew
(74) *Attorney, Agent, or Firm* — Dinsmore & Shohl LLP; Douglas J. McEvoy

(57) ABSTRACT

A joint implant assembly including a spherical shaped component adapted to securing to an end of a first joint defining bone and a recess shaped component adapted to securing to an end of a second joint defining bone. Each of the components establishes an opposing wear surface, at which microscopic sized particles build up over time resulting from prolonged use of the joint. At least one of the spherical and recess shaped components exhibits a plurality of interior entrapment chambers, each of which including a narrow-most entranceway location communicating with the wear surface. The entrapment chambers further exhibit outwardly widening capture profiles extending within the
(Continued)

associated component for securing volumes of the microscopic particles away from a zone defined between the wear surfaces.

11 Claims, 4 Drawing Sheets

Related U.S. Application Data continuation-in-part of application No. 12/266,695, filed on Nov. 7, 2008, now Pat. No. 8,979,938.

(60) Provisional application No. 61/825,551, filed on May 21, 2013, provisional application No. 61/183,736, filed on Jun. 3, 2009, provisional application No. 60/986,486, filed on Nov. 8, 2007.

(52) U.S. Cl.
CPC .......... *A61F 2/30965* (2013.01); *A61F 2/3804* (2013.01); *A61F 2002/30673* (2013.01); *A61F 2002/30682* (2013.01); *A61F 2002/30683* (2013.01); *A61F 2002/30685* (2013.01); *A61F 2002/30686* (2013.01); *A61F 2002/30807* (2013.01); *A61F 2002/30823* (2013.01); *A61F 2002/30827* (2013.01); *A61F 2002/30934* (2013.01); *A61F 2002/30937* (2013.01); *A61F 2002/30971* (2013.01)

(58) Field of Classification Search
USPC ..................................................... 623/22.17
See application file for complete search history.

(56) References Cited

U.S. PATENT DOCUMENTS

| | | | |
|---|---|---|---|
| 3,798,679 A | 3/1974 | Ewald | |
| 3,875,594 A | 4/1975 | Swanson | |
| 3,964,106 A | 6/1976 | Hutter, Jr. et al. | |
| 4,215,439 A | 8/1980 | Gold et al. | |
| 4,231,122 A | 11/1980 | Koeneman | |
| 4,328,593 A | 5/1982 | Sutter et al. | |
| 4,367,562 A | 1/1983 | Gauthier et al. | |
| 4,538,305 A | 9/1985 | Engelbrecht et al. | |
| 4,714,477 A | 12/1987 | Fichera et al. | |
| 4,950,298 A | 8/1990 | Gustilo et al. | |
| 4,964,868 A | 10/1990 | Bloebaum | |
| 4,990,161 A | 2/1991 | Kampner | |
| 5,007,934 A | 4/1991 | Stone | |
| 5,021,061 A | 6/1991 | Wevers et al. | |
| 5,092,898 A | 3/1992 | Bekki et al. | |
| 5,171,325 A | 12/1992 | Aulie | |
| 5,181,926 A * | 1/1993 | Koch | A61F 2/30 623/22.14 |
| 5,197,987 A | 3/1993 | Koch et al. | |
| 5,389,107 A | 2/1995 | Nassar et al. | |
| 5,462,362 A | 10/1995 | Yuhta et al. | |
| 5,509,934 A | 4/1996 | Cohen | |
| 5,514,182 A | 5/1996 | Shea | |
| 5,549,701 A | 8/1996 | Mikhail | |
| 5,553,476 A | 9/1996 | Oehy et al. | |
| 5,571,193 A | 11/1996 | Kampner | |
| 5,593,445 A | 1/1997 | Waits | |
| 5,645,601 A | 7/1997 | Pope et al. | |
| 5,662,158 A | 9/1997 | Caldarise | |
| 5,676,702 A | 10/1997 | Ratron et al. | |
| 5,702,476 A | 12/1997 | Limacher et al. | |
| 5,702,483 A | 12/1997 | Kwong | |
| 5,728,175 A | 3/1998 | Rincoe | |
| 5,800,566 A | 9/1998 | Gramnas et al. | |
| 5,879,406 A * | 3/1999 | Lilley | A61F 2/30771 623/22.15 |
| 5,879,407 A | 3/1999 | Waggener | |
| 5,916,269 A | 6/1999 | Serbousek et al. | |
| 5,921,358 A | 7/1999 | Gramnas et al. | |
| 6,008,431 A * | 12/1999 | Caldarise | A61F 2/30767 623/23.3 |
| 6,045,581 A | 4/2000 | Burkinshaw | |
| 6,165,223 A | 12/2000 | Metzger et al. | |
| 6,398,815 B1 | 6/2002 | Pope et al. | |
| 6,599,322 B1 * | 7/2003 | Amrich | A61F 2/30767 623/20.17 |
| 6,627,141 B2 | 9/2003 | McNulty et al. | |
| 6,660,040 B2 | 12/2003 | Chan et al. | |
| 6,692,679 B1 | 2/2004 | McNulty et al. | |
| 6,723,102 B2 | 4/2004 | Johnson et al. | |
| 6,800,298 B1 | 10/2004 | Burdick et al. | |
| 6,800,670 B2 | 10/2004 | Shen et al. | |
| 6,811,568 B2 | 11/2004 | Minamikawa | |
| 6,818,172 B2 | 11/2004 | King et al. | |
| 6,866,683 B2 | 3/2005 | Gerbec et al. | |
| 6,866,685 B2 | 3/2005 | Chan et al. | |
| 6,962,607 B2 | 11/2005 | Gundlapalli et al. | |
| 7,044,983 B1 | 5/2006 | Cheng et al. | |
| 7,066,958 B2 | 6/2006 | Ferree | |
| 7,077,867 B1 | 7/2006 | Pope et al. | |
| 7,087,091 B1 | 8/2006 | Chen et al. | |
| 7,109,181 B2 | 9/2006 | Cowlen et al. | |
| 7,148,209 B2 | 12/2006 | Hoemann et al. | |
| 7,175,666 B2 | 2/2007 | Yao | |
| 7,179,298 B2 | 2/2007 | Greenlee | |
| 7,186,364 B2 | 3/2007 | King et al. | |
| 7,331,995 B2 | 2/2008 | Eisermann et al. | |
| 7,384,430 B2 | 6/2008 | Greer et al. | |
| 7,578,851 B2 | 8/2009 | Dong et al. | |
| 7,758,653 B2 * | 7/2010 | Steinberg | A61C 8/00 623/22.19 |
| 7,771,485 B2 | 8/2010 | Grundei | |
| 7,780,738 B2 | 8/2010 | Khandkar et al. | |
| 8,070,823 B2 * | 12/2011 | Kellar | C23C 30/00 623/16.11 |
| 2002/0183845 A1 | 12/2002 | Mansmann | |
| 2003/0055508 A1 | 3/2003 | Metzger et al. | |
| 2003/0065401 A1 * | 4/2003 | Amrich | A61B 17/8085 623/23.55 |
| 2003/0114935 A1 | 6/2003 | Chan et al. | |
| 2003/0216669 A1 | 11/2003 | Lang et al. | |
| 2004/0024460 A1 | 2/2004 | Ferree | |
| 2004/0068322 A1 | 4/2004 | Ferree | |
| 2005/0055100 A1 | 3/2005 | Lewis et al. | |
| 2005/0171604 A1 | 8/2005 | Michalow | |
| 2005/0177248 A1 * | 8/2005 | Hall | A61C 8/0012 623/23.56 |
| 2005/0192672 A1 | 9/2005 | Wyss et al. | |
| 2005/0192674 A1 | 9/2005 | Ferree | |
| 2005/0202371 A1 | 9/2005 | McGuire | |
| 2005/0287187 A1 | 12/2005 | Mansmann | |
| 2006/0009857 A1 * | 1/2006 | Gibbs | A61F 2/32 623/23.4 |
| 2006/0015186 A1 | 1/2006 | Isaac | |
| 2006/0200247 A1 * | 9/2006 | Charrois | A61F 2/32 623/19.11 |
| 2007/0088442 A1 * | 4/2007 | Cima | A61B 5/055 623/18.11 |
| 2007/0179613 A1 | 8/2007 | Heinz | |
| 2007/0270975 A1 | 11/2007 | Taylor et al. | |
| 2007/0287027 A1 | 12/2007 | Justin et al. | |
| 2008/0033567 A1 | 2/2008 | Stchur | |
| 2008/0208428 A1 * | 8/2008 | Thompson | B60K 23/04 701/82 |
| 2008/0288081 A1 | 11/2008 | Scrafton et al. | |
| 2009/0076605 A1 | 3/2009 | Linares | |
| 2009/0112315 A1 | 4/2009 | Fang et al. | |
| 2009/0125108 A1 | 5/2009 | Linares | |
| 2010/0042214 A1 * | 2/2010 | Nebosky | A61B 17/56 623/16.11 |
| 2010/0161070 A1 * | 6/2010 | Gomaa | A61F 2/30 623/22.21 |
| 2010/0222892 A1 * | 9/2010 | Linares | A61F 2/30771 623/23.5 |

(56) References Cited

U.S. PATENT DOCUMENTS

| | | | | |
|---|---|---|---|---|
| 2011/0257757 A1* | 10/2011 | Popoola | ............... | A61F 2/32 623/22.15 |
| 2011/0313532 A1* | 12/2011 | Hunt | ............... | A61F 2/30767 623/18.11 |
| 2012/0221110 A1* | 8/2012 | Nakanishi | ........... | A61F 2/30771 623/18.11 |

* cited by examiner

HIP AND KNEE JOINT ASSEMBLIES INCORPORATING DEBRIS COLLECTION ARCHITECTURE BETWEEN THE BALL AND SEAT INTERFACE

CROSS-REFERENCE TO RELATED APPLICATIONS

This Application claims the benefit of U.S. Provisional Application 61/825,551 filed on May 21, 2013. This Application is a Continuation-in-part of application Ser. No. 12/776,903 filed on May 10, 2010. Application Ser. No. 12/776,903 claims the benefit of U.S. Provisional Application 61/183,736 filed on Jun. 3, 2009. Application Ser. No. 12/776,903 is a Continuation-in-part of application Ser. No. 12/266,695 filed on Nov. 7, 2008. Application Ser. No. 12/266,695 claims the benefit of U.S. Provisional Application 60/986,486 filed on Nov. 8, 2007, the contents of which are incorporated herein in their entirety.

FIELD OF THE INVENTION

The present invention relates generally to artificially implantable knee and hip joint assemblies. More specifically, the present invention discloses a variety of implant architectures in which an articulating and inter-abrading profile established between a ball and seat interface includes a plurality of individual debris collection chambers for facilitating secure removal of such as microscopic sized particles and shavings resulting from the articulating motion established between the ball and seat, the composition of which including any of a variety of different materials.

BACKGROUND OF THE INVENTION

The prior art is documented with numerous examples of artificial implant assemblies, such as which are constructed in the attempt to facilitate ease of articulation as well as to reduce long term wear. Examples of such implants include the wear reducing acetabular component of Serbousek U.S. Pat. No. 5,916,269 and prosthetic component of Chan, U.S. Pat. No. 6,866,685, each of which incorporate interruptions in the inter-articulating joint faces. Also noted is the passive lubricating prosthetic joint of Heinz, US 2007/0179613, along with the prosthesis constructions in Taylor, US 2007/0270975 and the ball joint or cap implant for an artificial hip joint depicted in Grundei U.S. Pat. No. 7,771,485.

A further objective of such artificial implant assemblies is the attempt to remove or isolate debris resulting from abrading contact and associated wear between the articulating surfaces of the joint implant. An example of one such construction is depicted in the debris isolating prosthetic hip joint of Kwong, U.S. Pat. No. 5,702,483 and which, in relevant part, incorporates a capsule configured by first and second surface treatments and in turn defined by the acetabular and femoral components. Each of the surface treatments causes fibrous tissue to attach to the acetabular and femoral components such that any resulting debris particles resulting from wearing of the articulating surfaces is confined within the capsule.

SUMMARY OF THE INVENTION

The present invention discloses a joint implant assembly including a spherical shaped component adapted to securing to an end of a first joint defining bone and a recess shaped component adapted to securing to an end of a second joint defining bone. Each of the components establishes an opposing wear surface, at which microscopic sized particles build up over time resulting from prolonged use of the joint.

At least one of the spherical and recess shaped components exhibits a plurality of interior entrapment chambers, each of which including a narrow-most entranceway location communicating with the wear surface. The entrapment chambers further exhibit outwardly widening capture profiles extending within the associated component for securing volumes of the microscopic particles away from a zone defined between the wear surfaces.

The implant assembly further includes at least one of a hip or knee joint assembly, in the instance of a hip joint, the assembly further exhibiting a concave shaped seat articulating relative to a spherical shaped ball mounted atop an affixing stem. In the instance of a knee joint, the assembly further exhibiting a concave seat attached to a pedestal supporting stem exhibiting debris capture architecture integrated into each of first and second lateral recessed locations, against which seat opposing and substantially spherical portions associated with an inter-articulating implant component forming a further portion of the knee joint assembly.

The entrapment chambers can further be constructed with any of individual pluralities of circular cross sectional profiles, continuous perimeter extending and coaxially spaced apart boundary profiles, angularly bisecting grid profiles, and ring shaped capture profiles. The spherical and recessed components can also constructed of at least one of a metal, plastic, ceramic or composite thereof.

BRIEF DESCRIPTION OF THE DRAWINGS

Reference will now be made to the attached drawings, when read in combination with the following detailed description, where in like reference numerals refer to like parts throughout the several views, and in which.

DETAILED DESCRIPTION OF THE PREFERRED EMBODIMENTS

As previously described, the present invention is directed to a variety of artificially implantable knee and hip joint assemblies, incorporating a variety of implant architectures. As will be further described in detail with regard to the following embodiments, the present invention focuses on an articulating and inter-abrading profile established between such as a ball and seat interface, in which progressive wear results in aggregation of microscopic sized debris particles (such as metal or plastic shavings). The ability to remove even a percentage of microscopic debris and particles from the inter-articulating wear zone defined between the articulating ball and concave seat, such as through the architectural design of the individual debris collection chambers as will be described in additional detail with reference to the succeeding illustrations, provides such artificial implants with greatly extended useful life and concurrent comfort to the patient.

Figure 1:
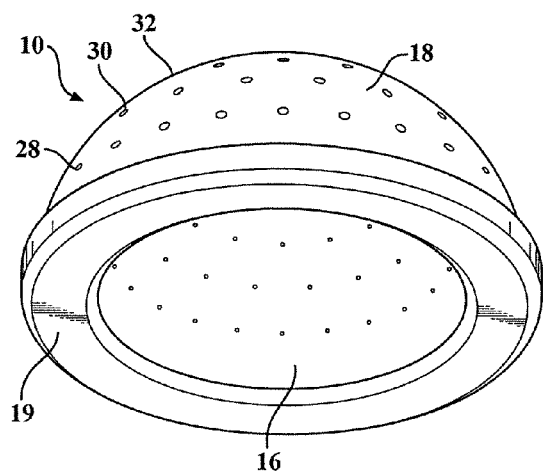
FIG. 1 is a perspective view of a concave seating component forming a portion of a hip joint implant assembly according to a first embodiment and which incorporates a first version of a debris collection architecture for removing microscopic shavings and particles from an inter-abrading and progressive wear profile established between the seat and an opposing ball.

Referring to FIG. 1, a perspective view is generally shown at 10 of a concave seating component forming a portion of a hip joint implant assembly according to a first embodiment. The component can include any material not limited to a plastic, metal or composite (it being understood that it is desirous in many instances to establish a wear profile between two different materials including plastic on metal but which can also envision plastic on plastic or metal on metal wear interfaces). In one non-limiting application the concave seating component 10 can include a first material (a polypropylene or other plastic), with an opposing ball or spherical component 12 (such as mounted to a stem 14 as shown in FIGS. 2-3) being constructed of a second alternating material (e.g. a titanium or other metal, ceramic or other suitable construction).

Figure 5:
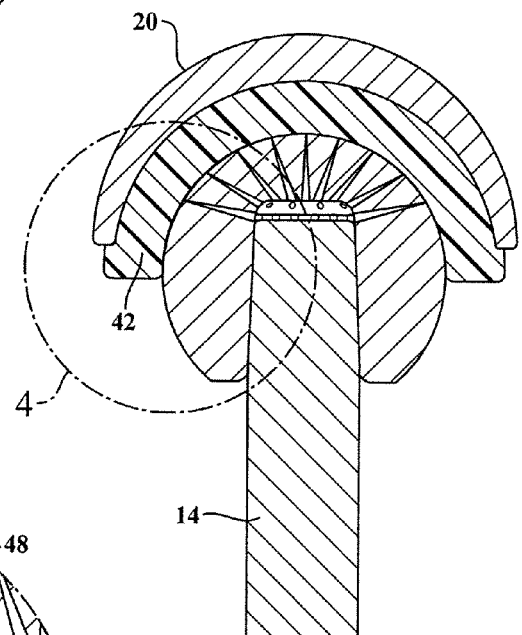
FIG. 5 is a plan view in cutaway of the ball in FIG. 4 in combination with a solid (non-apertured) concave seat.
Figure 6:
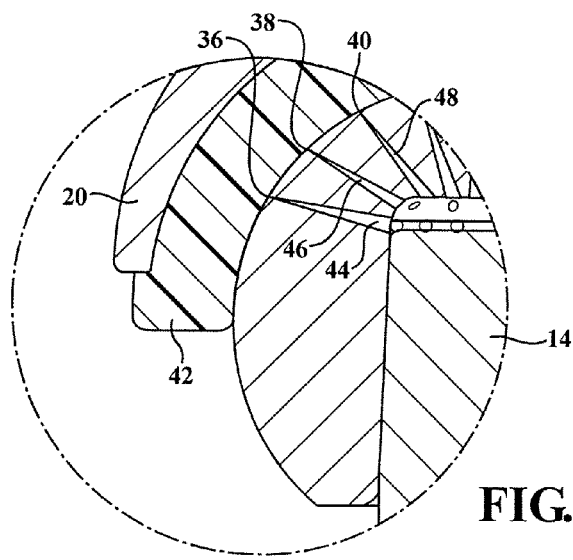
FIG. 6 is an enlarged partial view of FIG. 5 and better showing the configuration of the integrally formed and individual debris collection chambers defined in the spherical ball, such including narrow-most entranceway locations arranged at the abrading wear zone, with outwardly widening capture chambers extending toward a supporting stem to which the ball is affixed.
Figure 7:
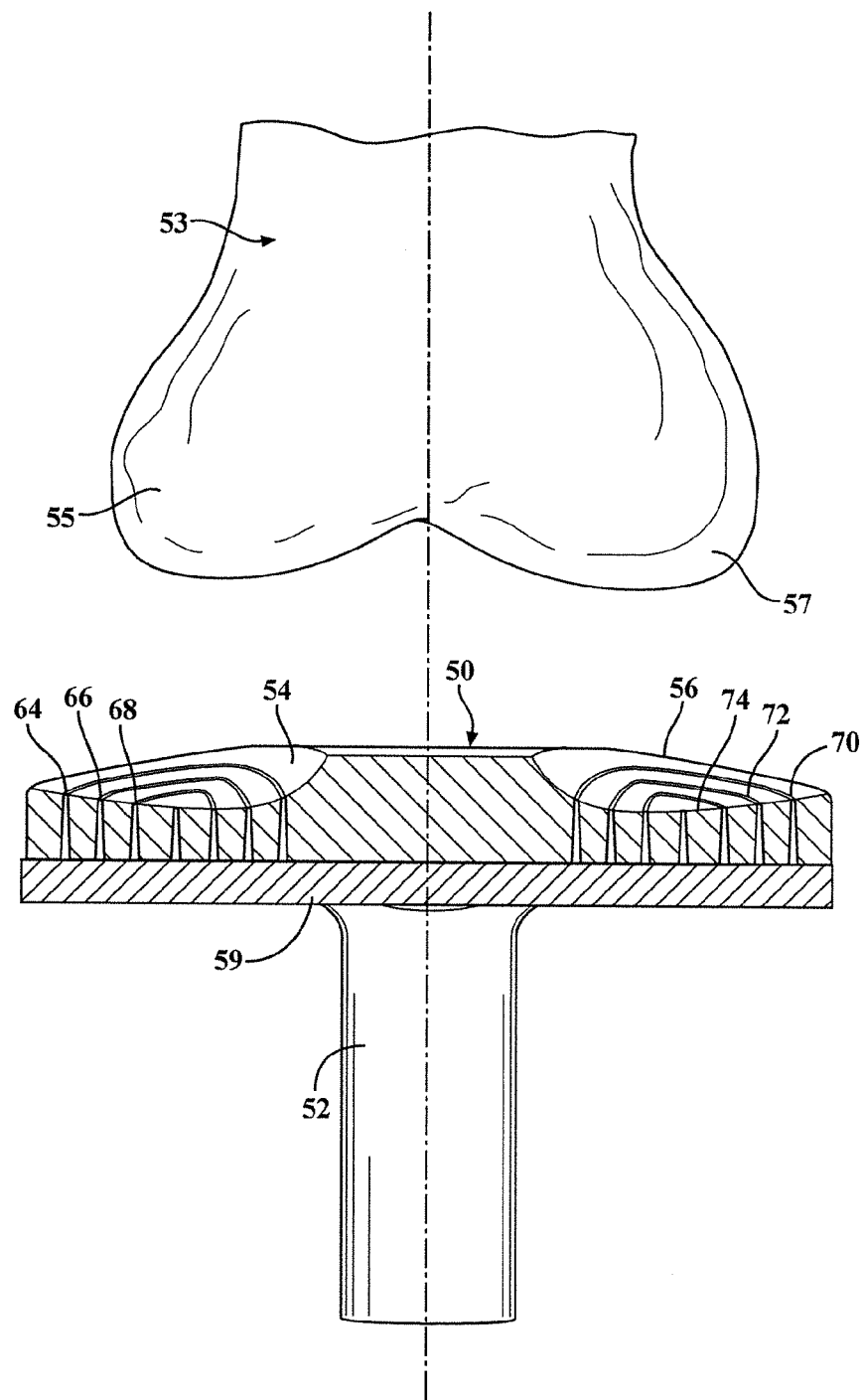
FIG. 7 is a plan view in cutaway of a concave seat component forming a portion of a knee joint implant according to a further embodiment and which exhibits a similar debris capture architecture integrated into each of first and second lateral recessed locations against which seat opposing and substantially spherical portions associated with an inter-articulating implant component.

Although not further shown, it is understood that the ball and seat elements associated with each of the hip joint variants of FIGS. 1-3 and 4-6, as well as the knee joint variant of FIGS. 7-8, are implanted in situ into reconditioned end surfaces of opposing bones during a suitable medical implantation procedure. Without limitation, it is further understood that the debris collection architecture as further described below can be incorporated into any wear profile associated with a joint assembly not limited to those specifically described and illustrated herein.

Figure 2:
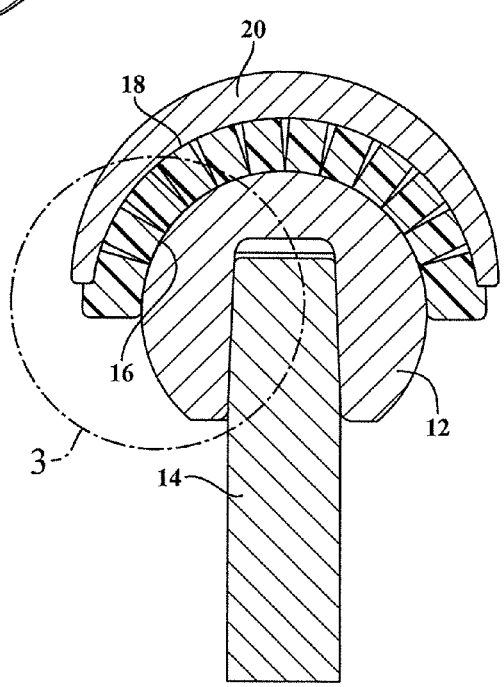
FIG. 2 is a plan view in cutaway of a spherical or ball shaped component and an opposing and inter-articulating concave seat such as depicted in FIG. 1.
Figure 3:
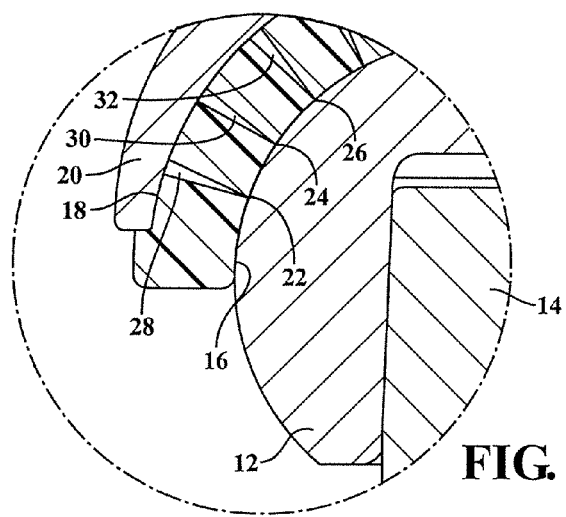
FIG. 3 is an enlarged partial view taken from FIG. 2 and better showing the configuration of the integrally formed and individual debris collection chambers defined in the concave seat, such including narrow-most entranceway locations communicating with the abrading wear zone, the individual collection chambers further exhibiting outwardly widening capture chambers extending in a generally outward radial fashion toward a metal substrate layer affixed to the concave seat.

Referring to FIGS. 1-3 collectively, a first version of a debris collection architecture includes a plurality of individual entrapment or capture chambers which are formed into the architecture of the concave seat and between an inner seating surface 16 and an outer (convex) surface 18 (these defining a generally consistent wall thickness further referenced by outer rim 19 in FIG. 1), over which in turn is mounted a substrate layer 20 (FIG. 2) such as a metal or other suitable material which defines an inner base support of the concave seat and which can be anchored or otherwise secured to a reconditioned recessed profile formed within the associated joint defining bone). As best shown in FIG. 3, the architecture of the individual entrapment chambers is further described and includes narrow-most entranceway locations (see circular or other polygonal cross sectional shaped profiles at 22, 24, 26, et seq. in FIG. 3) at the abrading wear zone, with outwardly widening capture profiles extending in a generally outwardly radial fashion toward the metal substrate layer 20 (see further at 28, 30, 32, et. seq.) affixed to the concave seat.

In this manner, the microscopic particles and shavings (e.g. metal or plastic) which are not shown but which are understood as inevitably resulting from the constant combined articulating and frictional/rubbing motion established between the spherical or ball shaped component and opposing concave seat component are usually of a microscopic dimension, thus enabling them to captured or retained within the narrowed openings 22-26 of the entrapment chambers, with additional captured particles gradually building up within each chamber toward the widened (outer) ends 28, 30, 32. It is further understood that the dimensions, shaping or other number of debris/particle capture chambers can be adjusted (such as from a generally conical shaped as generally depicted) and in order to adapt to varying operational parameters associated with the joint. These considerations can include without limitation the type of joint, the composition of the materials employed in the opposing components, and the anticipated size of the inevitable debris/particles which will be created within the joint/wear zone.

Figure 4:
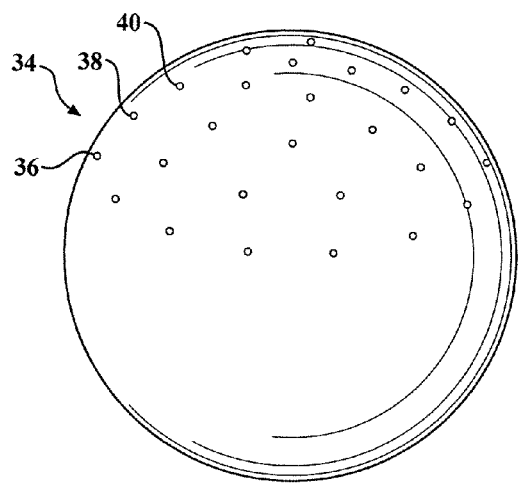
FIG. 4 is a perspective view of a spherical or ball component forming an opposing portion of a hip joint implant assembly according to a second embodiment and which incorporates another version of a debris collection architecture form incorporated into an inter-abrading and progressive wear profile established with an opposing concave seat.

FIGS. 4-6 illustrate a reverse embodiment as compared to FIGS. 1-3, see as generally shown at 34 in FIG. 4, and in which the debris capture architecture is configured within a redesigned ball or sphere forming a portion of a hip joint implant assembly according to a second embodiment. As with the first embodiment, a plurality of integrally formed and individual debris collection chambers are defined in the spherical ball, these best depicted in the enlarged cutaway of FIG. 6 and including narrow-most entranceway locations 36, 38, 40, et seq. at the abrading wear zone established with a surrounding concave seat 42, with outwardly widening capture chambers 44, 46, 48, et. seq. extending toward the stem 14 to which the ball is affixed.

Also, and as with the initial embodiment of FIGS. 1-3, the individual debris entrapment chambers can be distributed in any desired spatial manner across either or both of the opposing and inter-articulating convex and concave surfaces associated with the ball/sphere and seat, respectively. This can further include varying the number and distribution of the entrapment chambers, as well as additionally or alternatively varying the size or dimension of the debris isolation chambers (such further contemplating having both smaller and larger sized chambers arranged in an inter-mixed fashion in order to better capture and remove a desired percentage of the microscopic sized wear debris or particles).

It is also envisioned that subset numbers of the debris capture or isolation chambers can vary in other manners not limited by the present description and which can be designed to enhance ongoing and continues particle debris removal over the life of the artificial implant. Otherwise, the embodiment of FIGS. 4-6 operates identically to that previously described in FIGS. 1-3, with the exception that the progressive debris entrapment occurs along the inter-articulating surface of the ball/sphere 34 in FIG. 4, and as opposed to occurring at the concave seat 10 of FIG. 1.

Referring to FIG. 7, a plan view in cutaway is shown of a concave seat component 50 (this as shown attached to a pedestal supporting stem 52 which can be anchored into a reconditioned bone end) and forming a portion of a knee joint implant according to a further embodiment. As depicted, the seat component 50 exhibits a similar debris capture architecture integrated into each of first and second lateral recessed profiles or locations, see at 54 and 56 and against which seat opposing and substantially spherical or convex shaped portions (generally depicted at 53 with convex surfaces 55 and 57 in spatially arrayed fashion relative to the concave seat component 50) associated with an inter-articulating implant component forming a further portion of a knee joint assembly. The captures pockets referenced in FIG. 7 are shown extending to a supporting surface of a planar base component 59 formed with the stem 52, it being understood that the depth and shape of each capture pocket (such as which are defined by any of an inner sleeve shape or other closed polygonal, arcuate or circular cross sectional profile defined in the concave seat or ball) can vary without shape or limitation.

Finally, and referencing FIGS. 8A-8D, depicted are a series of non-limiting examples of concave seating components, such as shown in FIG. 7, with each successive seating component exhibiting a varying debris entrapment profile. These include, initially referring to FIG. 8A, a first variant 58 in which individual pluralities of debris entrapment chambers 60 and 62 similar to those previously depicted are formed into each of the laterally arrayed and recessed (or pseudo-concave) seating surfaces (corresponding to those shown at 564 and 56 in the variant of FIG. 7) and which again include narrowed diameter inlet locations proximate the joint wear interface for admitting or capturing the microscopic sized wear particles, with communicating and widening capture pockets extending inwardly into the body of the supporting component for securely retaining the volumes metal or plastic wear particulate.

Figure 8A:
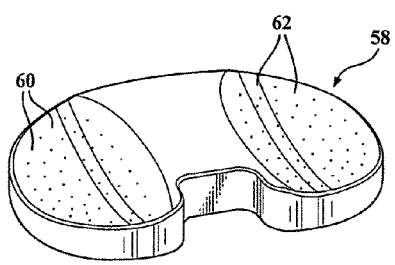
FIGS. 8A-8D depict in perspective a series of non-limiting examples of concave seating components, such as shown in FIG. 7, with each exhibiting a varying debris entrapment profile.
Figure 8B:
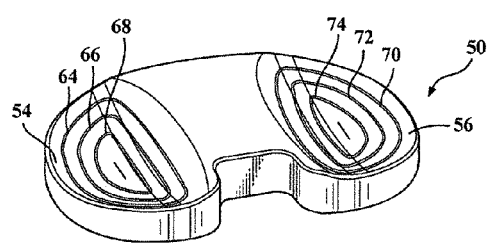

FIG. 8B depicts the variant shown at 50 in FIG. 7 and in which the entrapment chambers extend as continuous perimeter extending and generally concentrically spaced apart and individually perimeter defining and enclosing boundaries, see individual pluralities 64, 66, 68, et seq. and 70, 72, 74, et seq. respectively defined in the exposed and laterally arrayed and recessed/concave support surfaces of the seat 50. The concentric profile shown can include any of generally circular shaped or, as depicted, modified arcuate profiles.

Figure 8C:
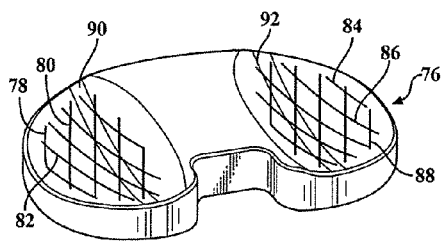
Figure 8D:
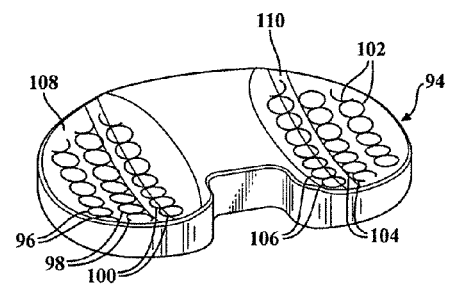

FIG. 8C depicts a yet further variant 76 in which angularly bisecting grid patterns, see individual pluralities of generally grid intersecting slots as depicted at 78, 80, 82, et seq. and 84, 86, 88, et seq. for each associated recessed concave seating surface, are respectively integrated into recessed support surfaces 90 and 92. Finally, FIG. 8D depicts an additional and non-limiting variant 94 in which pluralities of ring shaped capture profiles are defined at 96, 98, 100, et. seq. and 102, 104, 106, et. seq., in each of first and second recessed support surfaces 108 and 110. As further shown, the ring shaped entrapment chambers are shown in an intercommunicating arrangement along selected and arcuate extending boundary locations, it being understood that some or all of the profiles can be segregated or isolated in any fashion desired.

Having described our invention, other and additional preferred embodiments will become apparent to those skilled in the art to which it pertains, and without deviating from the scope of the appended claims.

We claim:

1. A joint implant assembly, comprising:
a spherical shaped component adapted to securing to an end of a first joint defining bone;
semi-spherical shaped component adapted to securing to an end of a second joint defining bone and within which is seated said spherical shaped component in inter-articulating supported fashion;
each of said components establishing an opposing wear surface at which microscopic sized particles abraded from said components build up over time resulting from prolonged use of said joint; and
a plurality of elongated and conical shaped entrapment chambers distributed across said semi-spherical shaped component, each of said chambers including a narrow-most diameter entranceway location communicating with said wear surface corresponding to a smallest diameter, said entrapment chambers each exhibiting progressively outwardly widening capture profiles extending away from said narrow-most entranceway locations through a first layer of said semi-spherical shaped component in an outwardly radial dispersed manner and so that a diameter of each of said entrapment chambers at any location farther away from said entranceway location is larger than a corresponding diameter at any location closer to said entranceway location, said entrapment chambers each terminating at a reverse surface of said first layer defining a thickness of said first layer in contact with a substrate mounting layer, such that a maximum diameter location of each entrapment chamber is located at an interface with said substrate layer for securing volumes of said microscopic particles passing through said narrow-most entranceway locations, and in order to segregate said particles away from a wear zone defined between said wear surfaces.

2. The implant assembly as described in claim 1, said implant assembly further comprising a hip joint assembly.

3. The implant assembly as described in claim 2, further comprising said spherical shaped component mounted atop an affixing stem.

4. The implant assembly as described in claim 1, said spherical and recessed components constructed of at least one of a metal, plastic, ceramic or composite thereof.

5. A joint implant assembly, comprising:
a spherical shaped component mounted atop a stem and adapted to securing to an end of a first joint defining bone;
a semi-spherical shaped component adapted to securing to an end of a second joint defining bone and within which is seated said spherical shaped component in inter-articulating supported fashion;
each of said components establishing an opposing wear surface at which microscopic sized particles abraded from said components build up over time resulting from prolonged use of said joint; and
a plurality of elongated and conical shaped entrapment chambers distributed across said spherical shaped component, each of said chambers including a narrow-most diameter entranceway locations communicating with said wear surface corresponding to a smallest diameter, said entrapment chambers each exhibiting progressively inwardly widening capture profiles extending away from said narrow-most entranceway locations and through said spherical shaped component and so that a diameter of each of said entrapment chambers at any location farther away from said entranceway location is larger than a corresponding diameter at any location closer to said entranceway location, said entrapment chambers each terminating at an opposite inner surface of said spherical shaped component defining a thickness thereof, said stem inserting into said inner surface of said spherical shaped component and so that said profiles are radially directed toward said stem, such that a maximum diameter location of each entrapment chamber is located at an interface with said stem for securing volumes of said microscopic particles passing through said narrow-most entranceway locations, and in order to segregate said particles away from a wear zone defined between said wear surfaces.

6. A joint implant assembly, comprising:

a concave seat component mounted to a pedestal supporting stem adapted to securing to a reconditioned end of a first joint defining bone, said concave seat component including a first exposed layer exhibiting first and second lateral recessed locations, said seat component further including a second planar base formed with said stem and upon which said concave seat is secured;

an inter-articulating component incorporated into a second joint defining bone and having a pair of convex end surfaces adapted to being received upon said lateral recessed locations of said first layer;

each of said components establishing an opposing wear surface at which microscopic sized particles abraded from said components build up over time resulting from prolonged use of said joint; and a plurality of elongated and conical shaped entrapment chambers distributed across each of said lateral recessed locations, each of said chambers including a narrow-most diameter entranceway locations communicating with said wear surface corresponding to a smallest diameter, said entrapment chambers each exhibiting progressively inwardly widening capture profiles extending away from said narrow-most entranceway locations and through said first exposed layer and so that a diameter of each of said entrapment chambers at any location farther away from said entranceway location is larger than a corresponding diameter at any location closer to said entranceway location, said entrapment chambers each terminating at a reverse surface of said exposed layer defining a thickness of said first layer in contact with said planar base, such that a maximum diameter location of each entrapment chamber is located at an interface with said planar base for securing volumes of said microscopic particles passing through said narrow-most entranceway locations, and in order to segregate said particles away from a wear zone defined between said wear surfaces.

7. The implant assembly as described in claim 6, further comprising said entrapment chambers each exhibiting circular or polygonal cross sectional profiles.

8. The implant assembly as described in claim 6, further comprising said entrapment chambers each exhibiting continuous perimeter extending and concentrically spaced apart boundary profiles.

9. The implant assembly as described in claim 6, further comprising said entrapment chambers each exhibiting linear and angularly bisecting grid profiles.

10. The implant assembly as described in claim 6, further comprising said entrapment chambers each exhibiting ring shaped capture profiles.

11. The implant assembly as described in claim 10, said ring shaped entrapment chambers intercommunicating along selected boundary locations.

\* \* \* \* \*